(12) United States Patent
Santos et al.

(10) Patent No.: US 10,463,621 B2
(45) Date of Patent: Nov. 5, 2019

(54) SPRAY DRYING PROCESS FOR PRODUCTION OF POWDERS WITH ENHANCED PROPERTIES

(71) Applicant: HOVIONE INTERNATIONAL LTD, Wanchai (CN)

(72) Inventors: José Luis Santos, Sintra (PT); Filipe Gaspar, Oeiras (PT); Marcio Temtem, Quinta do Conde (PT)

(73) Assignee: Hovione Holding Limited, Wanchai (HK)

( * ) Notice: Subject to any disclaimer, the term of this patent is extended or adjusted under 35 U.S.C. 154(b) by 158 days.

(21) Appl. No.: 15/280,423

(22) Filed: Sep. 29, 2016

(65) Prior Publication Data
US 2017/0014346 A1    Jan. 19, 2017

Related U.S. Application Data

(63) Continuation of application No. PCT/GB2015/050963, filed on Mar. 30, 2015.

(30) Foreign Application Priority Data

Mar. 31, 2014    (PT) .......................... 107568

(51) Int. Cl.
| | | |
|---|---|---|
| *A61K 9/16* | (2006.01) | |
| *B01D 1/18* | (2006.01) | |
| *B01J 2/04* | (2006.01) | |
| *F26B 3/12* | (2006.01) | |
| *A61K 31/496* | (2006.01) | |

(52) U.S. Cl.
CPC .......... *A61K 9/1682* (2013.01); *A61K 9/1635* (2013.01); *A61K 31/496* (2013.01); *B01D 1/18* (2013.01); *B01J 2/04* (2013.01); *F26B 3/12* (2013.01)

(58) Field of Classification Search
None
See application file for complete search history.

(56) References Cited

U.S. PATENT DOCUMENTS

| | | |
|---|---|---|
| 1,634,640 A | 7/1927 | Zizinia |
| 1,782,054 A | 11/1930 | Uhl |
| (Continued) | | |

FOREIGN PATENT DOCUMENTS

| | | |
|---|---|---|
| CN | 1726009 A | 1/2006 |
| CN | 1726076 A | 1/2006 |
| (Continued) | | |

OTHER PUBLICATIONS

Foreign Communication from a related application—Examination Report No. 1 of Australian Patent Application No. 2015242444, dated Feb. 2, 2018, 3 pages.
(Continued)

*Primary Examiner* — Mary Lynn F Theisen
(74) *Attorney, Agent, or Firm* — Conley Rose, P.C.; Rodney B. Carroll

(57) ABSTRACT

An improved spray drying method for production of amorphous solid dispersions with enhanced bulk density and material attributes comprising the introduction of at least one additional stream in at least one of multiple locations in a spray dryer without interfering with the spray region.

25 Claims, 2 Drawing Sheets

(56) References Cited

U.S. PATENT DOCUMENTS

| | | | | |
|---|---|---|---|---|
| 2,829,710 A * | 4/1958 | Paasch | ............... | B01D 1/18 159/4.4 |
| 2,901,435 A * | 8/1959 | Robson | ............... | B01D 1/18 252/186.2 |
| 2,911,036 A * | 11/1959 | Lazar | ............... | A23B 5/035 159/4.01 |
| 3,895,994 A | 7/1975 | Saguchi et al. | | |
| 5,596,817 A | 1/1997 | Hansen | | |
| 8,337,895 B2 | 12/2012 | Bennett et al. | | |
| 2003/0163931 A1* | 9/2003 | Beyerinck | ............... | A61K 9/146 34/372 |
| 2004/0118007 A1* | 6/2004 | Chickering, III | .... | A61K 9/1647 34/360 |
| 2007/0218012 A1 | 9/2007 | Bittorf et al. | | |
| 2010/0011610 A1* | 1/2010 | Bittorf | ............... | F26B 3/08 34/359 |
| 2010/0119587 A1 | 5/2010 | Amighi et al. | | |
| 2013/0009330 A1* | 1/2013 | Fragale | ............... | A61K 9/0019 264/12 |
| 2014/0284001 A1* | 9/2014 | Amstad | ............... | F26B 3/12 159/4.01 |
| 2016/0051956 A1* | 2/2016 | Penth | ............... | B01D 9/0054 516/7 |

FOREIGN PATENT DOCUMENTS

| | | |
|---|---|---|
| CN | 1745170 A | 3/2006 |
| EP | 0387950 A1 | 9/1990 |
| EP | 0571684 A1 | 12/1993 |
| EP | 0610040 A1 | 8/1994 |
| EP | 0818224 A2 | 1/1998 |
| JP | H966201 A | 3/1997 |
| JP | 2012509922 A | 4/2012 |
| PT | 107568 | 3/2014 |
| WO | 200064552 | 11/2000 |
| WO | 2003090893 A1 | 11/2003 |
| WO | 2004058156 A2 | 7/2004 |
| WO | 2011154014 A1 | 12/2011 |
| WO | 2013150090 A1 | 10/2013 |
| WO | 2015150763 A1 | 10/2015 |

OTHER PUBLICATIONS

Foreign Communication from a related application—First Office Action of Chinese Patent Application No. 201580023071.6, dated Apr. 18, 2018, with English translation, 15 pages.

Foreign Communication from Priority Application—International Search Report and Written Opinion of PCT/GB2015/050963 dated Jul. 7, 2015, 11pages.

Foreign Communication from Priority Application—Written Opinion of the International Preliminary Examining Authority of PCT/GB2015/050963 dated Jul. 6, 2016, 5 pages.

Masters, K., "Spray Drying, An Introduction to Principles, Operational Practice and Applications," Chemical and Process Engineering Series, Sep. 30, 1991, Longman, 5th Edition, Leonard Hill Books, London (3 pages of cover and publishing information).

Foreign Communication from a priority application—Search Report of Portuguese Application No. 107568 dated Apr. 21, 2014, 5 pages.

Foreign Communication from a related application—Second Office Action of Chinese Patent Application No. 201580023071.6, dated Dec. 12, 2018, with English translation, 5 pages.

Foreign Communication from a related application—Office Action of Japanese Application No. 2016-559916, dated Dec. 4, 2018, with English translation, 9 pages.

Zoryu Benran, May 30, 1975, 1st edition, 1st issue, pp. 211-248 (in Japanese language).

* cited by examiner

SPRAY DRYING PROCESS FOR PRODUCTION OF POWDERS WITH ENHANCED PROPERTIES

CROSS-REFERENCE TO RELATED APPLICATIONS

The present application is a continuation of and claims priority to International Application No. PCT/GB2015/050963 filed Mar. 30, 2015, entitled "Improved Spray Drying Process for Production of Powders with Enhanced Properties," which claims priority to Portuguese Application No. 107568 filed Mar. 31, 2014, which applications are incorporated by reference herein in their entirety.

FIELD OF INVENTION

The present invention is in the technical field of drying methods. More particularly, the present invention is in the technical field of spray drying applied to active pharmaceutical ingredients (APIs), drug product intermediates and drug products.

BACKGROUND OF THE INVENTION

Conventional operation of the spray dryers used in the pharmaceutical industry use solely the drying gas to dry and pneumatically transport the dried powder to a cyclone and/or filter bag [Masters, K. "Spray drying handbook." (1991)]. Often the drying conditions required to obtain the desired attributes (e.g. density, particle size) restrict process throughput and/or lead to materials that have a higher than desirable solvent/water content which may pose a stability problem, particularly in the processing of amorphous solid dispersions. Also, the use of very high throughputs of feed solution often leads to condensation problems and accumulation of material on the walls of the equipment when spray drying high boiling point solvents such as water.

In spray dried dispersions (SDD) the active pharmaceutical ingredient (API) is molecularly dispersed in a polymeric matrix. The polymer is used to stabilize the amorphous and metastable form of the drug and also to sustain supersaturation of the API in solution/biological fluids, thereby increasing bioavailability. The inherent use of solvents in spray drying processes contributes to a plasticization effect and correspondent undesirable decrease of the glass transition temperature (Tg) of amorphous solid dispersions during the drying process. The Tg is one of the most important attributes of an amorphous solid dispersion since it can be intrinsically related with the API molecular mobility and is one of the characteristics that dictates whether a spray dried dispersion formulation is stable enough to prevent crystallization over the shelf-life of the product.

Typical operations downstream to the spray drying step in a pharmaceutical process include blending, roller compaction and tableting or capsule filling. The ability for a SDD material to flow and be processed in the downstream equipment with no major operational difficulties is closely related to powder properties, namely particle size, density and cohesive—adhesive forces balance between the ingredients and equipment. Rule-of-thumb strategies for improving flow indicate that both particle size and density should be as large as possible. On a best-case scenario, the powder would also have the necessary compressibility (indicated by the relation between bulk and tap density) to enable a direct compression approach.

The spray drying literature includes a number of examples where additional streams of fluids are added to the process train with the aim of reducing wall accumulation. For example, U.S. Pat. No. 5,596,817 discloses a process where product deposition is minimized by injection of high velocity and low flow rate gas in the top of the drying chamber and near the chamber walls, enabling an efficient sweeping effect. U.S. Pat. No. 3,895,994 also discloses a spray drying process where product deposits on the cylinder wall and their recirculation into the high temperature zone are minimized through the introduction of tangential gas streams from the inlets arranged around the discharge end of the cylinder of spray dryer so as to swirl within said cylinder. However, neither of these patents specifically discuss problems associated with spray drying to produce amorphous solid dispersions of active pharmaceutical ingredients and polymers. The additional gas streams in these patents are used simply to minimize solid deposits forming on the walls of the spray dryers, and not to provide enhanced powder properties.

The state-of-the-art also includes a number of examples where a modified spray dryer setup was used to optimize powder properties. For example, EP patent application 0387950 discloses a device for obtaining a spray-dried product of predetermined bulk density. The nozzle is surrounded by a tube supplying a gas with dry particulate material. The ratio and speed of collision between the gas-solid suspension and spray enables the control of powder bulk density. WO 2011/154014 discloses a spray drying process where the drying gas supplied to the chamber is enriched in one or more solvent vapors to adjust the properties of the particles, namely their density and solvent content.

U.S. Pat. No. 8,337,895 discloses a process mostly intended for inhalation products that comprises a conditioning zone with controlled humidity and temperature to modulate droplet drying and promote surface enrichment of the active components, and a drying zone to dry the droplets exiting the conditioning zone. The conditioning zone comprises humidity control, for example through an humid air inlet, and/or temperature controller to control the conditions in the conditioning zone so that the droplets dry more slowly in the conditioning zone than in the dryer.

According to this disclosure, the drying kinetics may be used to facilitate surface diffusion of surface active components, facilitating amorphous-to-crystalline transformations during the manufacture of dry powder formulations.

In summary, the state-of-the-art only discloses strategies to prevent deposition of product on the walls of the equipment, or the adjustment of powder properties with the introduction of additional solvents or significant changes in atomization and process train configuration.

The inventors of the present invention have appreciated that there is a need for simpler spray drying processes capable of producing materials with higher bulk density, without compromising the process throughput, yield and more important the quality of the product, particularly its amorphous content. In particular, the inventors have appreciated that for spray drying processes for the production of amorphous solid dispersions of active pharmaceutical ingredients and polymers, there is a need to produce spray dried particles with enhanced powder properties such as increased bulk density, lower glass transition temperature and lower residual solvent content. Furthermore, the inventors have appreciated that there is a need to provide spray dried powders with such properties with a simple spray drying process. Although prior art attempts to improve spray dried product properties are known, these processes are complex and typically involve the use of foreign solvents in the drying gas or the introduction of solid material near the atomizer (WO2011/154014 and EP0387950), or the use of controlling drying kinetics with multiple chambers in a spray dryer such as separate conditioning and drying chambers (U.S. Pat. No. 8,337,895). The invention herein disclosed overcomes the shortcomings identified in the prior art.

SUMMARY OF THE INVENTION

According to an aspect of the invention, there is provided a spray drying process, which process comprises the steps of:
  a. providing a feed mixture comprising: one or more active pharmaceutical ingredients (APIs), one or more excipients, or mixtures thereof; and a solvent system comprising at least one solvent;
  b. feeding said feed mixture to a spray drying apparatus comprising a spray dryer chamber;
  c. atomizing said feed mixture into droplets using an atomization nozzle;
  d. drying said droplets with a drying gas to produce particles of said one or more APIs; one or more excipients, or mixtures thereof
  e. feeding one or more secondary gas streams to the spray drying apparatus in at least one of multiple locations in the spray drying apparatus;
  f. recovering said particles from the spray dryer chamber.

Preferably, the feed mixture comprises one or more APIs and one or more excipients. Preferably, the one or more excipients comprise one or more polymers.

Preferably, step d. of the process comprises producing amorphous solid dispersions of the one or more APIs and, if present, one or more excipients. Preferably, the process is for producing amorphous solid dispersions with increased bulk density, relative to a corresponding spray drying process where step e. of claim 1 is not present.

Preferably, step f. comprises recovering said particles from the spray dryer chamber by recovering said particles in a container connected to the spray dryer chamber. More preferably, step f. of recovering said particles from the spray dryer chamber comprises said particles passing through a cyclone or filter bag connected to the spray dryer chamber into a container connected to the cyclone or filter bag.

According to another aspect of the invention, there is provided, a spray drying apparatus comprising at least one secondary gas stream inlet in at least one of multiple locations in the spray drying apparatus.

Preferably, the apparatus is for producing solid dispersions with increased bulk density relative to a corresponding spray drying apparatus that does not comprise secondary gas stream inlets.

According to another aspect of the invention, there is provided the use of a process of the invention to increase the bulk density of an amorphous solid dispersion of an active pharmaceutical ingredient (API) and one or more excipients relative to a corresponding process where one or more secondary gas streams are not present, to increase the amorphous physical stability of the particles recovered from the spray dryer chamber relative to a corresponding process where one or more secondary gas streams are not present, and/or to decrease the residual solvent content of the particles recovered from the spray dryer chamber relative to a corresponding process where one or more secondary gas streams are not present.

According to another aspect of the invention, there is provided an amorphous solid dispersion comprising at least one active pharmaceutical ingredient (API) and at least one excipient obtainable by the process of the invention.

According to another aspect of the invention, there is provided an amorphous solid dispersion comprising at least one active pharmaceutical ingredient (API) and at least one excipient wherein the amorphous solid dispersion has a bulk density of greater than 0.07 g/ml. Preferably, the dispersion has a bulk density of greater than 0.1 g/ml, and optionally greater than 0.15 g/ml. Preferably, the dispersion has a bulk density of from 0.1 g/ml to 0.5 g/ml, or from 0.1 g/ml to 0.5 g/ml. Preferably, the at least one excipient comprises a polymer.

The present invention is an improved spray drying method for production of pharmaceutical compositions, and particularly amorphous solid dispersions, with enhanced throughput and enhanced material attributes. At least one additional stream of gas is added in at least one of multiple positions in a spray drying apparatus without interfering with the spray region, which enables the improvement of the process throughput, powder density, and amorphous physical stability due to a reduction of residual solvent content. The powder properties of the spray dried product are controlled through the location of the one or more secondary gas streams (optimized to avoid interfering with the spray region), feed rate and temperature of the secondary gas streams.

The present invention uses the introduction of secondary gas streams to locally decrease saturation, reducing the solvent content in pharmaceutical formulations such as amorphous solid dispersions produced by spray drying, reducing the plasticization effect and thus the undesirable changes in the amorphous content.

It was found that the powder bulk density can be further increased by i) introducing the additional stream of gas further away from the spray region, by ii) increasing the flow rate of the additional stream of gas, and by iii) decreasing the temperature of the additional stream of gas.

The process of the present invention provides spray dried amorphous solid dispersions with increased bulk density, a lower glass transition temperature, and/or a lower residual solvent content in the spray dried product relative to a corresponding process where one or more secondary gas streams are not used.

The terms "corresponding process wherein the one or more secondary gas streams are not present", and "corresponding spray drying process" and similar such terms as used herein refer to an identical spray drying process with the exception that the secondary gas streams (for example, process step e.) are not present. Thus, for example, when describing a spray drying process as "corresponding to another spray drying process but where no step e. is present", this refers to an identical spray drying process using identical apparatus, and identical spray drying conditions, the only difference between the two processes being the presence of the one or more secondary gas streams. By "spray region" we mean the volume within the spray drying chamber containing the vast majority of the droplets, located below the atomizer.

The term "bulk density" as used herein is a familiar term of art, and refers to the density of a bulk material such as a powder that may have different size particles, with irregular sized voids between the different particles. Bulk density is defined as the total mass of a sample of the material divided by the total volume of the material.

DETAILED DESCRIPTION OF THE INVENTION

Figure 1:
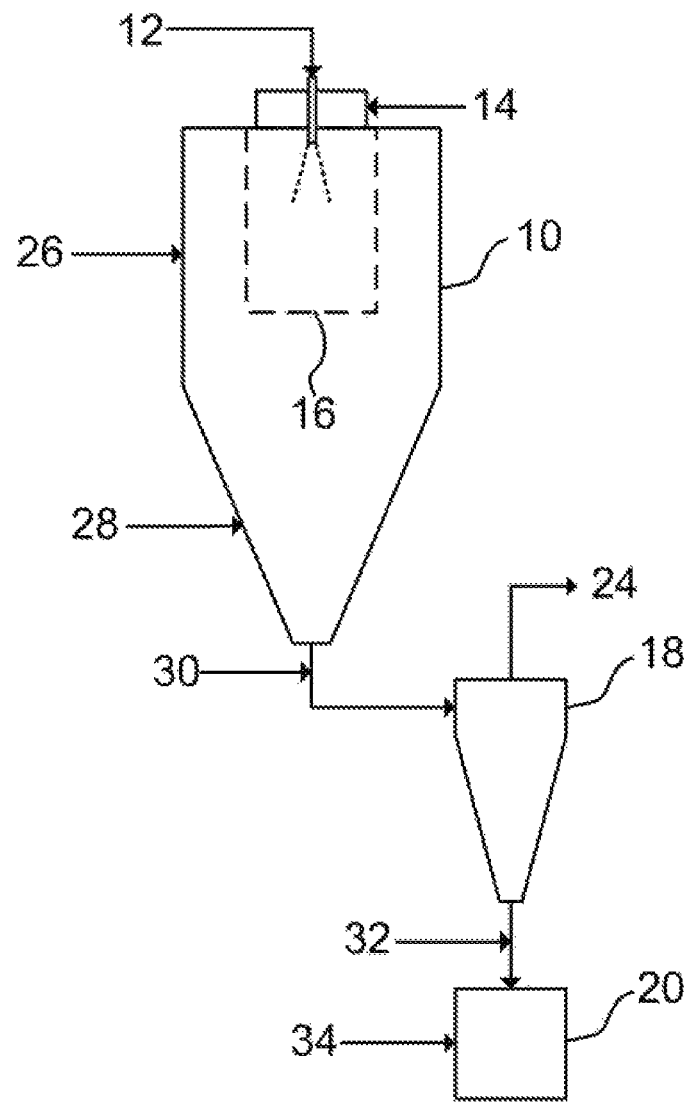
FIG. 1 is a diagram of the process of the present invention.

Referring now to the invention in more detail, in FIG. 1 it is shown a spray drying apparatus comprising a spray dryer chamber 10 where a feed mixture in the form of a liquid stream 12 is atomized into droplets in an atomization nozzle and dried with drying gas 14, which is preferably a co-current drying gas. The properties of the dried particles are mostly defined in a region 16 in the vicinity of the nozzle, hereafter referred to as the spray region. The spray region 16 is where the majority of the dried particles are formed. The spray drying apparatus also comprises means for recovering the dried particles from the spray dryer chamber. In FIG. 1, the dried particles are separated from the drying gas in a cyclone 18 and collected in a container 20, while the drying gas exits the cyclone in an outlet stream 24. However, the means for recovering dried particles from the spray dryer chamber may also take the form of other means, which will be known to the person skilled in the art, such as a filter bag.

The spray dryer chamber shown in FIG. 1 preferably comprises a cylindrical upper section and a conical lower section, relative to the drying gas outlet. However, alternative spray dryer chamber shapes and types are also within the scope of the invention. Such suitable alternatives will be known to the skilled person.

The spray dryer chamber also preferably comprises an atomization nozzle of the pressure type, of the two-fluid type, or of the rotary type. The atomization nozzle is preferably centrally located in the top of the spray dryer chamber.

One or more secondary gas streams are added to the process train. Preferably, the one or more secondary gas stream are added to the spray drying apparatus in at least one of the following locations: i) in the straight section of the spray dryer chamber (location 26); ii) in the conical section of the drying chamber (location 28); iii) in the connection between the drying chamber and the cyclone (location 30); iv) in the connection between the cyclone and the solids container (location 32); and v) in the solids container (location 34). However, other locations in the spray drying apparatus for adding the one or more secondary gas streams are not excluded from the scope of the invention.

In an example, the location of the one or more secondary gas streams can be selected depending on what the intended purpose of the one or more gas streams is. For example, it may be desirable to use the one or more secondary gas streams to prevent condensation of the spray dried product in the coldest parts of the spray drying apparatus such as in locations 30, 32 and/or 34, by adding the one or more secondary gas streams in these locations.

In more detail, still referring to the embodiment of the invention discussed in FIG. 1, the flow rate and the temperature of the secondary gas stream added to the process train in any of the locations 26, 28, 30, 32 and 34 can be adjusted independently to meet the desired effect depending on the flow rate and temperature of the liquid stream 12 and drying gas 14. In particular, the flow rate of the stream added in location 34 can be adjusted in a range that at its upper limit promotes the fluidization of the powder in the solids container 20 while preventing the powder to backflow upwards to the cyclone.

In further detail, still referring to the embodiment of the invention of FIG. 1, the liquid stream 12 comprises a solvent system which can be comprised of one solvent, or mixture of solvents. The liquid stream 12 also comprises at least one active pharmaceutical ingredient, or at least one excipient, and preferentially at least one excipient and at least one API. The solvent or solvent mixture in stream 12 can be water, organic solvents, or combinations thereof. Preferably, the solvent system comprises water, acetone, methyl ethyl ketone, ethanol, methanol, isopropanol, ethyl acetate, hexane, heptane, dichloromethane, tetrahydrofuran, or a combination thereof. Upon contact with the drying gas 14 the drying of the droplets of feed mixture produces amorphous solid dispersions of the active pharmaceutical ingredients in the excipients. The atomization system can be of pressure-type, two-fluid-type (either internal or external mixture), rotary-type or any other atomization mechanism known by one skilled in the art.

Preferably, the one or more excipients comprise one or more polymers. Preferably, a solution of one or more active pharmaceutical ingredients and one or more polymers is spray dried to produce an amorphous solid dispersion of the one or more active pharmaceutical ingredients in the one or more polymers. Polymers suitable for use in the formulations of the disclosure include, but are not limited to, N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, polysaccharide, homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, graft copolymer of polyethylene glycol/polyvinyl caprolactam/polyvinyl acetate (e.g., Soluplus®), polyvinylpyrrolidone, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), alkyl acrylate Crosspolymers (e.g. Permulen® Carbopol®), acrylic acid polymer crosslinked with divinyl glycol (e.g. Noveon®), Gelatin, gelatin, copolymer of vinyl acetate and crotonic acid, partially hydrolyzed polyvinyl acetate, carrageenan, galactomannan, high viscosity gums or xanthan gum, or a combination thereof.

The advantages of the present invention include, without limitation, that it enables the production of high density powders owing to the ability of having very high relative saturation of the drying gas in the spray region without compromising the process yield. High density powders are known to facilitate downstream processes of pharmaceutical operations such for example tableting, capsule filling or sachet filling.

It was found that the powder bulk density can be increased if the additional stream of gas is introduced with increasing distance away from the spray region. Other effects that were identified were that bulk density can be increased by increasing the flow rate of the additional stream of gas, and by decreasing the temperature of the additional stream of gas.

In a specific example, to maximize the bulk density of a spray dried powder, such as a spray dried amorphous solid dispersion, the distance between one of the one or more secondary gas stream inlets and the atomization nozzle is from 20 cm to 70 cm, optionally from 20 to 45 cm, or from 45 to 70 cm.

The bulk density of the spray dried amorphous solid dispersion can also be maximized in certain processes by using one or more secondary gas streams with a temperature of from 25° C. to 75° C., preferably from 25° C. to 50° C.

The bulk density of the spray dried amorphous solid dispersion can also be maximized in certain processes by using one or more secondary gas streams with a flow rate of from 50 litres per minute to 100 litres per minute, such as from 60 litres per minute to 90 litres per minute.

In certain processes, the flow rate of the drying gas into the spray dryer chamber is from 12 kg/hour to 35 kg/hour, such as from 12 kg/hour to 24 kg/hour, or from 12 kg/hour to 20 kg/hour.

The feed mixture can be fed to the spray dryer chamber at any suitable flow rate to achieve optimum spray drying and optimum powder properties. In certain processes, the feed mixture is fed to the spray drying apparatus with a feed rate of from 20 to 30 ml/minute.

In a specific example, the bulk density of the spray dried powder such as a spray dried amorphous solid dispersion is maximized with a distance between the one or more secondary gas stream inlets and the atomization nozzle of from 20 cm to 70 cm, a flow rate of the one or more secondary gas streams of from 50 litres per minute to 100 litres per minute, and a temperature of the one or more secondary gas streams of from 25° C. to 50° C.

The drying gas can be any suitable drying gas known in the art to effectively dry atomized droplets of a feed mixture. Preferably, the drying gas is nitrogen. The one or more secondary gas streams can also comprise any suitable drying gas known in the art to be suitable for use in spray drying processes. Preferably, the one or more secondary gas streams comprise nitrogen.

The process of the present invention provides spray dried particles such as spray dried amorphous solid dispersions of one or more APIs and one or more excipients such as polymers with a bulk density of greater than 0.07 g/ml, preferably, greater than 0.15 g/ml. Preferably, the bulk density of spray dried particles is from 0.1 g/ml to 0.5 g ml, or from 0.1 g/ml to 0.25 g/ml.

In addition to increased bulk density, the produced particles such as amorphous solid dispersions of one or more APIs and one or more excipients such as polymers have improved amorphous physical stability when compared to a conventional corresponding spray drying process where step e. of using the one or more secondary gas streams is not present, since in the present invention these particles are only exposed to high relative saturations for a smaller period of time. The present invention also enables the use of throughputs of feed solution higher than in conventional spray drying, while minimizing typical condensation problems when spray drying high boiling point solvents such as water, or accumulation of the material on the walls of the equipment. It also enhances the cyclone efficiency through an adequate balancing of the flow rate of the added gas streams. An additional benefit of the present invention is that it can reduce the residual solvent of the powders produced since these are exposed to lower relative saturations in the collector owing to the added gas streams.

The advantages of the present invention include, without limitation, that:

- it enables the production of high density powders owing to the ability of having very high relative saturation of the drying gas in the spray region (region 16) without compromising the process yield. High density powders are known to facilitate downstream processes such as for example tableting and capsule filling.
- Additionally, the produced particles have improved amorphous physical stability when compared to a conventional corresponding spray drying process where step e. of using the one or more secondary gas stream is not present, since in the present invention these particles are only exposed to high relative saturations for a smaller period of time.
- The present invention enables the use of very high throughputs of feed solution, while minimizing typical condensation problems when spray drying high boiling point solvents such as water, or accumulation of the material on the walls of the equipment.
- It also enhances the cyclone efficiency through an adequate balancing of the flow rate of the added gas streams.
- An additional benefit of the present invention is that it can reduce the residual solvent of the powders produced since these are exposed to lower relative saturations in the collector owing to the added gas streams.

Furthermore, the process of the present invention provides the advantages discussed above by employing a simpler process than prior art attempts to optimize properties of spray dried powders. For example, the process of the present invention preferably does not involve introduction of solid material to the spray dryer chamber such as particles of solid material dispersed within the drying gas. The process of the invention also only requires the use of one solvent system which is the solvent system employed in the feed mixture. The process of the present invention preferably does not comprise additional solvent vapours being introduced to the spray drying process train. For example, preferably, the drying gas does not comprise solvent vapours. The process of the present invention also preferably comprises atomizing the feed mixture into droplets and drying of said droplets with a drying gas, wherein the atomization and drying occurs within the same chamber, such as spray dryer chamber 10.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

EXAMPLES

Example 1

This example demonstrates the impact of process conditions on the production of an amorphous solid dispersion of itraconazole (API) in copovidone (polymer) using the invention herein presented.

Five trials were carried out using a half factorial design of experiments (DoE) (trials #3 to #7). The variables selected in the design of experiment were the location of the added gas stream in relation to the nozzle (20 cm to 70 cm), the feed rate (60 to 90 L/min), and the temperature (25° C. to 75° C.) of the added gas stream. For comparison purposes, one trial was carried out using feasible operating conditions of a conventional spray drying setup (trial #1), without using an additional nitrogen stream. The same throughput used in trials #3 to #7 was used in trial #2 in conventional spray drying mode of operation.

A feed mixture was prepared in each trial by dissolving 2 g of API and 18 g of polymer in a mixture of acetone:water with a 75:25 w/w ratio (735 g of acetone and 245 g of water).

|  |  | Trial | | | | | | |
|---|---|---|---|---|---|---|---|---|
|  |  | 1 | 2 | 3 | 4 | 5 | 6 | 7 |
| Operating conditions | | | | | | | | |
| N2_location | cm | — | — | 70 | 70 | 20 | 20 | 45 |
| F_add | L/min | — | — | 60 | 90 | 90 | 60 | 75 |
| T_add | ° C. | — | — | 25 | 75 | 25 | 75 | 50 |
| Relative throughput[a] | — | 1 | 2 | 2 | 2 | 2 | 2 | 2 |
| F_drying | kg/h | 24 | 12 | 12 | 12 | 12 | 12 | 12 |
| F_feed | mL/min | 24 | 24 | 24 | 24 | 24 | 24 | 24 |
| F_atomiz | L/min | 30 | 30 | 30 | 30 | 30 | 30 | 30 |
| T_in | ° C. | 90 | 110 | 110 | 110 | 110 | 110 | 110 |
| T_out | ° C. | 25 | NA | 21 | 30 | 17 | 27 | 23 |
| T_dew | ° C. | 15 | 26 | 26 | 26 | 26 | 26 | 26 |
| T_dew* | ° C. | — | — | 21 | 20 | 20 | 21 | 20 |
| Results | | | | | | | | |
| Bulk density | g/mL | 0.065 | NA | 0.129 | 0.164 | 0.160 | 0.093 | 0.120 |
| Tg | ° C. | 50 | NA | 39 | 46 | 46 | 42 | 45 |

[a]Relative throughput is determined by comparing the ratio of F_feed and F_drying in each trial to to trial #1

A laboratory scale spray dryer (Procept 4M8Trix) equipped with a two-fluid nozzle was used to process the feed mixture at 24 mL/min, with an atomization nitrogen flow rate of 30 L/min. An additional stream of neat nitrogen was added in radially evenly distributed points, tangential to the wall of the drying chamber.

The operating conditions are detailed in the table below. Of note is the drying gas flow rate used in the trials. In trial #1 the minimum drying gas flow rate that could be used to overcome condensation issues was 24 kg/h (the drying gas flow rate was increased in a stepwise fashion until no condensation was observed). The process throughput was increased in trial #2 by reducing the drying gas flow rate to 12 kg/h, which led to condensation and sticking of the solids to the equipment walls. Hence, the results show that an increase in process throughput as in trial #2 is unfeasible in a conventional spray drying process setup.

Figure 2:
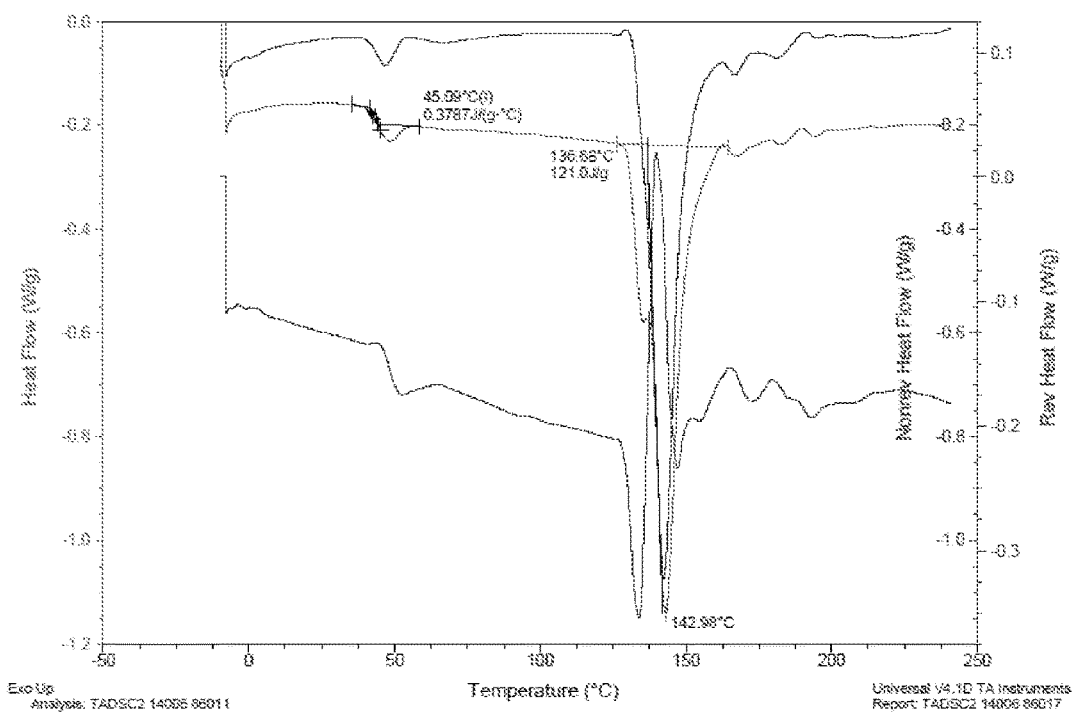
FIG. 2 is a DSC thermogram of the powder obtained in trial #8.

In the trials of the DoE, the use of an additional nitrogen stream enabled the use of a drying gas flow rate of 12 kg/h and consequently an increase in the local relative saturation conditions in the spray region. The use of an additional stream of nitrogen had an effect of lowering the process dew point (compiled in the table below as T_dew*), which reduced the potential for condensation. Amorphous materials were obtained in all trials in the DoE (#3 to #7), which is indicated by a single glass transition temperature in the DSC analysis (see FIG. 2 related to trial #7). In contrast, amorphous material could not be obtained in conventional spray drying mode in trial #2 due to condensation issues.

The bulk density of the amorphous solid dispersion produced after spray drying was 0.065 g/mL in trial #1. In the DoE trials where an additional stream of nitrogen was added to the process train, bulk density was always larger than in trial #1. The highest bulk density value was observed in trial #4 (0.165 g/mL), with more than a two-fold increase in relation to trial #1. Hence, the use of an improved spray drying process as wherein disclosed enables an increase in bulk density for a fixed mixture feed rate.

The analysis of the results obtained in the DoE trials shows that bulk density increases with increasing distance of the added stream in regards to the spray region (N2_location), with increasing flow rate of the added stream (F_add), and with decreasing temperature of the added stream (T_add).

What is claimed is:

1. A spray drying process, which process comprises the steps of:
  a. providing a feed mixture comprising: one or more active pharmaceutical ingredients (APIs), one or more excipients, or mixtures thereof; and a solvent system comprising at least one solvent;
  b. feeding said feed mixture to a spray drying apparatus comprising a spray dryer chamber having a cylindrical upper section and a conical lower section, the conical lower section further having an outlet, wherein the spray drying apparatus does not have one or more fluidized chambers located proximate the outlet; does not have one or more associated gas streams providing fluidizing gas to the one or more fluidized chambers; and does not have a gas stream associated with a return of fine material to the spray dryer chamber;
  c. atomizing said feed mixture into droplets using an atomization nozzle;
  d. drying said droplets with a drying gas to produce particles of said one or more APIs, one or more excipients, or mixtures thereof;
  e. feeding one or more secondary gas streams to the spray drying apparatus in at least one of multiple locations in the spray drying apparatus, wherein the at least one of multiple locations is selected from the group consisting of:
    (i) in the cylindrical upper section of the spray dryer chamber (location 26);
    (ii) in the conical section of the spray dryer chamber (location 28);

(iii) in a connection between the spray dryer chamber and a filter bag or cyclone (location 30);
(iv) in a connection between the filter bag or cyclone and a container (location 32);
(v) in the container (location 34);
(vi) in a location between the spray dryer chamber and the container if no cyclone or filter bag is present; and
(vii) combinations thereof;

f. recovering said particles from the spray dryer chamber through the use of a cyclone or filter bag connected to the outlet of the conical lower section.

2. The spray drying process according to claim 1, wherein the feed mixture comprises one or more active pharmaceutical ingredients and one or more excipients.

3. The spray drying process according to claim 1, wherein the process comprises producing amorphous solid dispersions of the one or more APIs, the one or more excipients, or the one or more APIs and one or more excipients.

4. The spray drying process according to claim 1, wherein the one or more excipients comprise one or more polymers.

5. The spray drying process according to claim 1, wherein the one or more excipients comprise N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, polysaccharide, homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, graft copolymer of polyethylene glycol/polyvinyl caprolactam/polyvinyl acetate, polyvinylpyrrolidone, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), alkyl acrylate Crosspolymers, acrylic acid polymer crosslinked with divinyl glycol, gelatin, copolymer of vinyl acetate and crotonic acid, partially hydrolyzed polyvinyl acetate, carrageenan, galactomannan, high viscosity gums, xanthan gum, or a combination thereof.

6. The spray drying process according to claim 1, wherein step f. of recovering said particles from the spray dryer chamber comprises recovering said particles in the container which is connected to the outlet of the conical lower section.

7. The spray drying process according to claim 1, wherein step f. of recovering said particles from the spray dryer chamber comprises said particles passing through the cyclone or filter bag connected to the outlet of the conical lower section into the container which is connected to the cyclone or filter bag.

8. The spray drying process according to claim 1, wherein the step e) comprises feeding at least one secondary gas stream in at least one of the following locations:
i) in the cylindrical upper section of the spray dryer chamber (location 26); or
ii) in the conical section of the spray dryer chamber (location 28).

9. The spray drying process according to claim 1, wherein the step e) comprises feeding at least one secondary gas stream in at least one of the following locations;

iii) in the connection between the spray dryer chamber and the filter bag or cyclone (location 30);
iv) in the connection between the filter bag or cyclone and the container (location 32);
v) in the container (location 34); or
vi) in a location between the spray dryer chamber and the container if no cyclone or filter bag is present.

10. The spray drying process according to claim 1, wherein the atomization nozzle is of the pressure type, of the two-fluid type, or of the rotary type.

11. The spray drying process according to claim 1, wherein the atomization nozzle is centrally located in the top of the spray dryer chamber.

12. The spray drying process according to claim 1, wherein the solvent system comprises water, organic solvents, acetone, methyl ethyl ketone, ethanol, methanol, isopropanol, ethyl acetate, hexane, heptane, dichloromethane, tetrahydrofuran or any combination thereof.

13. The spray drying process according to claim 1, wherein the secondary gas streams are added to the spray drying apparatus in a location outside the spray region.

14. The spray drying process according to claim 1, wherein the stream exiting the spray dryer chamber has a reduced relative solvent saturation in relation to a corresponding conventional spray drying process without additional gas streams.

15. The spray drying process according to claim 1, wherein the bulk density of the spray dried particles is further increased by any of the following options:
i) increasing the distance of the added stream to the spray region;
ii) increasing the flow rate of the added stream;
iii) decreasing the temperature of the added stream.

16. The spray drying process according to claim 1, wherein the throughput to the spray dryer is higher than in a corresponding conventional spray drying process, wherein step e. of claim 1 is not present.

17. The spray drying process according to claim 1, wherein the one or more secondary gas streams and/or the drying gas comprises a nitrogen gas stream.

18. The spray drying process according to claim 1, wherein the bulk density of the recovered particles is greater than 0.07 g/ml.

19. The spray drying process according to claim 1, wherein the bulk density of the recovered particles is greater than 0.1 g/ml, optionally greater than 0.15 g/ml.

20. The spray drying process according to claim 1, wherein the bulk density of the recovered particles is from 0.1 g/ml to 0.25 g/ml.

21. The spray drying process according to claim 1, wherein the bulk density of the recovered particles is from 0.1 g/ml to 0.5 g/ml.

22. The spray drying process according to claim 1, wherein the process does not involve introduction of solid material to the spray dryer chamber, or solid particulate material dispersed within the drying gas.

23. The spray drying process according to claim 1, wherein the only solvent system used in the process is the one in the feed mixture in which the one or more APIs; one or more excipients, or mixtures thereof, are dissolved.

24. The spray drying process according to claim 1, wherein the drying gas does not comprise any solvent vapours.

25. The spray drying process according to claim 1, wherein atomization of the feed mixture into droplets, and drying of the droplets to produce spray dried particles occurs within the same chamber.

* * * * *